(12) United States Patent
Redmond et al.

(10) Patent No.: US 8,431,142 B2
(45) Date of Patent: Apr. 30, 2013

(54) TOPICAL SANITIZING GEL CONTAINING AVENANTHRAMIDES

(75) Inventors: Mark James Redmond, Edmonton (CA); Joseph H. Neuser, Green Bay, WI (US)

(73) Assignee: The Idea Folder, LLC, Green Bay, WI (US)

( * ) Notice: Subject to any disclaimer, the term of this patent is extended or adjusted under 35 U.S.C. 154(b) by 20 days.

(21) Appl. No.: 13/117,767

(22) Filed: May 27, 2011

(65) Prior Publication Data
US 2012/0294911 A1 Nov. 22, 2012

Related U.S. Application Data

(60) Provisional application No. 61/487,340, filed on May 18, 2011.

(51) Int. Cl.
- *A61K 8/02* (2006.01)
- *A01N 25/00* (2006.01)
- *A01N 31/00* (2006.01)

(52) U.S. Cl.
USPC .......................... 424/405; 424/401; 514/724

(58) Field of Classification Search .................. None
See application file for complete search history.

(56) References Cited

U.S. PATENT DOCUMENTS

| | | | |
|---|---|---|---|
| 3,059,241 A | 10/1962 | O'Brien et al. | |
| 3,942,193 A | 3/1976 | Pugh | |
| 4,853,978 A | 8/1989 | Stockum | |
| 5,014,362 A | 5/1991 | Tillotson et al. | |
| 5,133,090 A | 7/1992 | Modak et al. | |
| 5,219,340 A | 6/1993 | Seneca | |
| 5,534,350 A | 7/1996 | Liou | |
| 5,641,494 A * | 6/1997 | Cauwenbergh | 424/401 |
| 5,691,287 A | 11/1997 | Villars et al. | |
| 5,830,884 A | 11/1998 | Kasica et al. | |
| 6,000,061 A | 12/1999 | Taneja et al. | |
| 6,953,582 B2 | 10/2005 | Chou | |
| 7,691,436 B2 | 4/2010 | Neuser et al. | |
| 7,718,240 B2 | 5/2010 | Neuser et al. | |
| 7,740,622 B2 | 6/2010 | Neuser et al. | |
| 2008/0268077 A1 * | 10/2008 | Vielhaber | 424/756 |
| 2010/0229281 A1 | 9/2010 | Neuser et al. | |
| 2012/0214878 A1 * | 8/2012 | Korb et al. | 514/724 |

OTHER PUBLICATIONS

RD 505011 A, May 2006.*
Becker, "Use of Colloidal Oatmeal Inside Rubber Gloves", AMA Archives of Dermatology, 1955:71(), p. 378 (1955).
Sompayrac et al., "Colloidal Oatmeal in Atopic Dermatitis of the Young", Journal of the Florida Medical Association, vol. 45 No. 12 p. 1411-1412, (Jun. 1959).

(Continued)

*Primary Examiner* — Carlos Azpuru
*Assistant Examiner* — Casey Hagopian
(74) *Attorney, Agent, or Firm* — Martin & Associates, LLC; Derek P. Martin

(57) ABSTRACT

Topical sanitizer includes avenanthramides, which is an active component of oats that is beneficial to the skin. The topical sanitizer is used preferably in conjunction with gloves that have an inner coating that includes avenanthramides. By using topical sanitizer that includes avenanthramides before and after wearing gloves, the skin of the person wearing the glove is more exposed to the beneficial avenanthramides all during the workday, not just when wearing gloves. The result is healthier, much softer and more comfortable skin on the hands.

4 Claims, 8 Drawing Sheets

OTHER PUBLICATIONS

White et al., "Colloidal Oatmeal as Dusting Powder for Surgical Gloves", Modern Hospital, vol. 93, No. 4, p. 129-130 (Oct. 1959).

Feigenbaum, "Colloidal Oatmeal for Skin Eruptions", Journal of the Medical Society of New Jersey, vol. 54, No. 7, p. 330-331 (Jul. 1957).

Grais, "Role of Colloidal Oatmeal in Dermatologic Treatment of the Aged", A.M.A. Archives of Dermatology and Syphilology, vol. 68 No. 4 p. 402-407 (Oct. 1953).

Yiu et al, Abstract, "Effect of Cooking on Starch and Beta-Glucan of Rolled Oats", Cereal Chem. 64, p. 373-379 (1987).

Hamann, "Review of Natural Rubber Latex Protein Allergy", American Journal of Contact Dermatitis, vol. 4 No. 1, p. 1 and 5 (1993).

"The Only Glove Powdered with Oats", Ostar glove brochure (1997).

Swanson et al, "Latex Allergen Affinity for Starch Powders Applied to Natural Rubber Gloves and Released as an Aerosol: From Dust to Don", Canadian Journal of Allergy and Clinical Immunology, vol. 5 No. 8, p. 330-336 (2000).

Henry Schein Dental '97 Catalog, p. 158 showing advertisement for Ultravena Ostar latex exam gloves that contain Oat Starch (1997).

Ultravena, "The Natural Solution to Skin Irritation for the Health Care Professional" (1994).

* cited by examiner

TOPICAL SANITIZING GEL CONTAINING AVENANTHRAMIDES

BACKGROUND

1. Technical Field

This disclosure generally relates to skin conditioning and protecting items, and more specifically relates to a topical sanitizer, glove and system that conditions and treats the skin on a person's hands.

2. Background Art

Many people must wear gloves for most or all of their workday to protect from environmental challenges including infectious diseases, for example, bacteria, viruses, or other contamination. For example, many doctors, nurses, dentists, clean room operators, food production and food service workers, sanitation workers, chemical plant workers, nuclear plant workers, welders, etc. wear gloves most of the day. Many people are required to change gloves many times a day. The most common type of protective gloves are latex and nitrile disposable gloves.

While latex gloves have been used for decades, they have significant drawbacks. For example, putting on latex gloves can be difficult because the latex has a tendency to bind to and stick to a person's skin. To make gloves easier to don (put on), latex gloves were made that included a cornstarch powder on the interior surface of the glove. The cornstarch powder made the glove much less likely to stick to a person's skin, and therefor greatly enhanced the ease of donning gloves. However, the cornstarch powder can serve as a carrier for allergens in latex, causing greater irritation to a person who has a sensitivity or allergy to latex. Many other powders were developed as alternatives to cornstarch powder for use on gloves.

One significant problem with powdered gloves is they cannot be used in many circumstances. For example, a surgeon cannot wear powdered gloves for fear of the powder dropping into the surgical site. Because there are many situations where powdered gloves are not allowed or are not preferred, various powder-free gloves have been developed.

A problem encountered by many people who wear protective gloves for most of the workday is skin irritation. The gloves trap perspiration on the skin and do not allow air flow that would normally help to evaporate the perspiration, thereby subjecting a person's hands to a damp or wet environment for most of the day. This can lead to skin irritation. The types of skin irritation caused by protective gloves have been well-documented over the years.

In an attempt to create gloves that are more friendly to the hands or a human who wears the gloves, various coatings for gloves have been developed over the years. For example, coatings that include aloe vera, oat starch, colloidal oatmeal, and beta glucan have been developed. Each of these has different properties and different beneficial effects. Note that some of these coatings are in a powder form, while others are powder-free.

Gloves that have coatings that are good for the skin are helpful when wearing the glove, but are not beneficial once the gloves have been removed and discarded. When a person removes a glove, the person typically cleanses his or her hands. When the person needs to put on a new pair of gloves, the person typically cleanses his or her hands again, then puts on the new pair of gloves. For hand-washing, common soaps have harsh detergents that have a tendency to dry out the skin by removing the oil on the skin. The repeated cleansing between glove changes can dry out a person's skin and cause various skin problems. The benefit of wearing gloves that include coatings that are beneficial to the skin may be reduced considerably by the repeated cleansing of the hands during the workday.

BRIEF SUMMARY

Topical sanitizer includes avenanthramides, which is an active component of oats that is beneficial to the skin. The topical sanitizer is used preferably in conjunction with gloves that have an inner coating that includes avenanthramides. By using topical sanitizer that includes avenanthramides before and after wearing gloves, the skin of the person wearing the glove is more exposed to the beneficial avenanthramides all during the workday, not just when wearing gloves. The result is much healthier, softer and more comfortable skin on the hands. A healthy skin offers superior protection to environmental challenges and disease.

The foregoing and other features and advantages will be apparent from the following more particular description, as illustrated in the accompanying drawings.

BRIEF DESCRIPTION OF THE SEVERAL VIEWS OF THE DRAWING(S)

The disclosure will be described in conjunction with the appended drawings, where like designations denote like elements, and:

DETAILED DESCRIPTION

Figure 1:
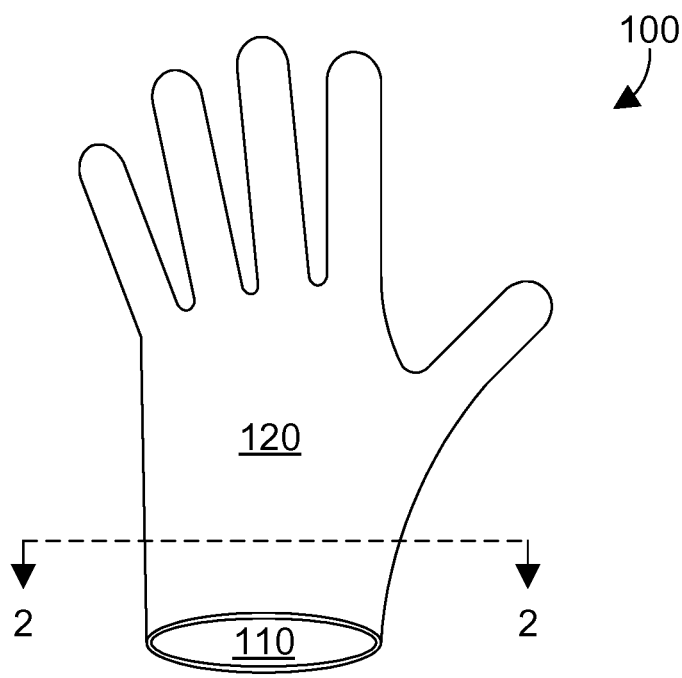
FIG. 1 is a perspective view of an elastomeric glove.
Figure 2:
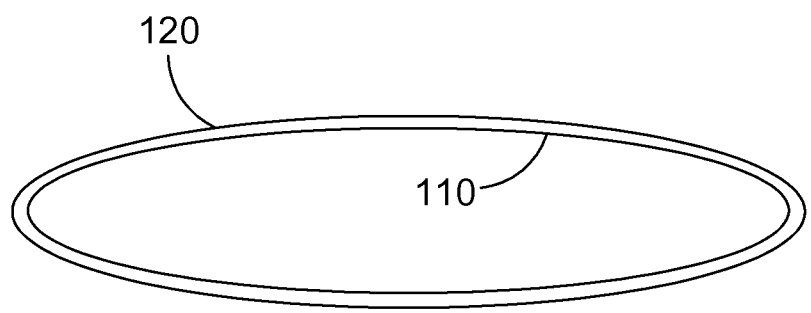
FIG. 2 is an enlarged cross-sectional view of the elastomeric glove shown in FIG. 1 taken along the line 2-2.

A sample glove 100 is shown in FIG. 1. Glove 100 could be made of any suitable material including latex, nitrile, polyvinyl chloride, neoprene, polyvinyl alcohol, butyl laminated film, DuPont Viton butyl, etc. In addition, various woven gloves are used in a variety of applications and are lined with many different materials, including DuPont Kevlar, nylon, lycra, terry, jersey, flocked fabric, polyester/cotton felt, woven knits, and interlocking knits. The disclosure and claims herein expressly extend to any suitable glove, whether disposable or not. Glove 100 includes an interior skin-contacting portion 110 and an exterior portion 120. This is shown in more detail in FIG. 2. In the past, various powders have been applied to the interior portion 110 of gloves, including talc, cornstarch, oat starch and colloidal oatmeal. Other powder-free coatings have also been used.

Figure 3:
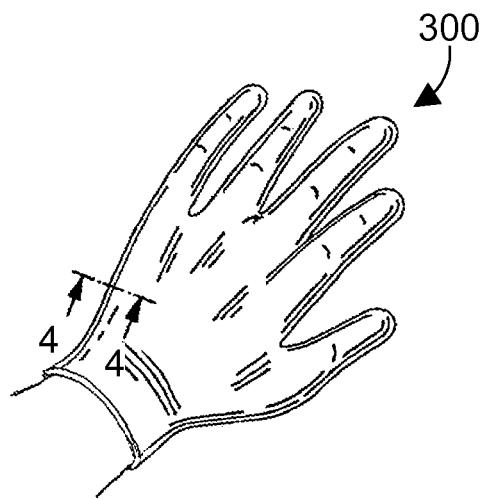
FIG. 3 is a perspective view of an elastomeric glove on a person's hand.
Figure 4:
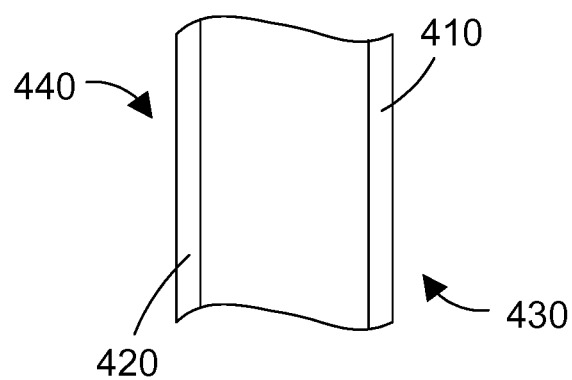
FIG. 4 is a cross-sectional view of the side wall of the elastomeric glove shown in FIG. 3 taken along the line 4-4.

FIGS. 3 and 4 illustrate a powder free glove 300. Glove 300 includes an inner cavity that defines an inner surface 430 that contacts the wearer's hand and an outer surface 440, as shown in FIG. 4. Either or both of surfaces 430 and 440 may include a dry coating, shown in FIG. 4 as a layer 410 on the inner surface 430 and a layer 420 on the outer surface 440. Note that layer 420 on outer surface 440 is optional for some glove applications, but many manufacturing methods for applying coating layer 410 to the inner surface 430 may also produce a residual coating layer 420 on the outer surface 440 as well. As used herein, "powder free" means that the gloves, on average, have less than 2 milligrams of particulate, when tested according to ASTM D6124.

As stated in the Background Art section above, wearing gloves all day long can be hard on the skin of a person's hands. The gloves trap moisture on the skin and inhibit air flow that prevents the normal evaporation of the moisture on the skin. As a result, many people who use gloves extensively develop various forms of contact dermatitis, or skin irritation, that is caused by the gloves. Needless to say, subjecting already irritated skin to repeated irritations every day can create greater irritation. Sites of irritation may lead to a breakdown of the protective barrier role of the skin leaving the person vulnerable to infection. With many people whose jobs require they wear gloves, they are left with few options for preventing or treating skin problems that result from wearing the gloves.

One way to potentially improve the problem of skin irritation due to wearing gloves is to use gloves with a coating that is beneficial to the skin. Some dry powders have been developed, such as oat starch and colloidal oatmeal, which are effective in delivering beneficial components of oats to a person's hand while wearing the glove. But powdered coatings cannot be used or are not preferred in many applications. Other powder-free coatings have been developed, which are also effective in delivering substances that are beneficial to skin to the hand of the person who uses the glove, such as aloe vera and beta glucan.

While providing powdered or powder-free coatings on gloves can help to soothe and treat a person's skin when wearing the glove, once the person takes off the gloves, the person typically cleansing his or her hands, which may remove most of the beneficial components the glove coating left on the skin. Many people such as healthcare professionals must put on and take off gloves dozens of times each day, cleansing their hands before and after they take off gloves. Many soaps include harsh detergents that remove most of the natural oils in the outer layers of skin. Thus, repeated washings throughout the workday cause the effect of drying out and irritating the skin, thereby limiting the benefit of the coatings on the gloves.

The problem of skin irritation created by extensive hand washing are alleviated by the disclosure and claims herein. A topical sanitizer contains avenanthramides, which are a component of oats that has great benefits for the skin. As used herein, the term "sanitizer" refers to a substance that cleanses the skin and kills germs. Recent research has shown that avenanthramides are the components in oats that provide anti-irritant properties to skin. Avenanthramides may be extracted from oats using any suitable process, including the process disclosed in U.S. Pat. No. 6,818,232 issued on Nov. 16, 2004 to Redmond et al. The topical sanitizer may be a foam soap, so a person who is used to washing his or her hands before donning gloves and after removing gloves can continue the normal routine by substituting the foam soap for the normal soap, and by substituting gloves that include a coating of avenanthramides on the inner skin-contacting surface of the gloves. In the alternative, the topical sanitizer may be an alcohol-based gel or an alcohol-free foam. These allow a person to cleanse and sanitize his or her hands before donning gloves and after removing gloves without washing with water. The topical sanitizers disclosed herein contain relatively low levels of detergent to avoid drying out the skin, in addition to avenanthramides to treat the skin, and may also optionally include zinc as a skin protectant. When a person sanitizes his or her hands with the topical sanitizer disclosed herein, the result is a residual coating of avenanthramides on the skin, which provides great benefit to the skin. Thus, the invention disclosed herein allows a person constantly to have avenanthramides on his or her skin, whether wearing gloves or not. The result is a significant decrease in skin irritation on a person's hands that would normally occur from extensive wearing of gloves.

Figure 5:
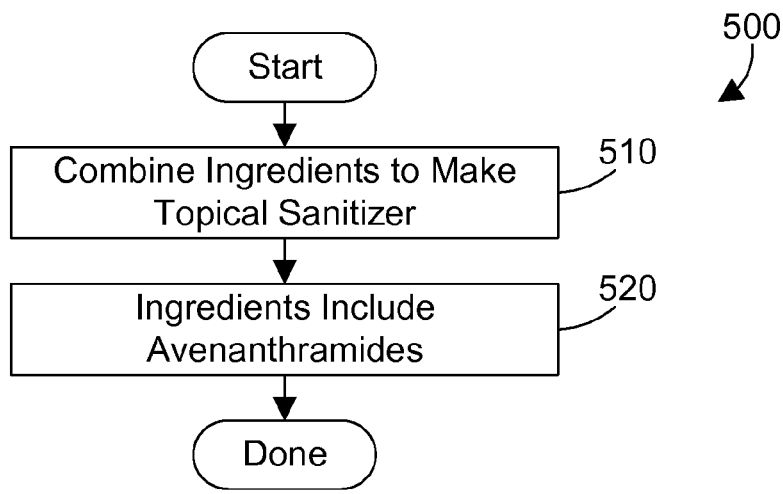
FIG. 5 is a flow diagram of a method for making topical sanitizer that includes avenanthramides.

Referring to FIG. 5, a method 500 combines ingredients to make a topical sanitizer (step 510). These ingredients include avenanthramides (step 520), and may also include zinc. Note the term "topical sanitizer" means any substance that includes avenanthramides that may be used to sanitize a person's hands, including without limitations gels, foams, soaps, etc. The disclosure and claims herein expressly details three specific embodiments of topical sanitizer, namely alcohol-based gel, foam soap, and alcohol-free foam.

Figure 6:
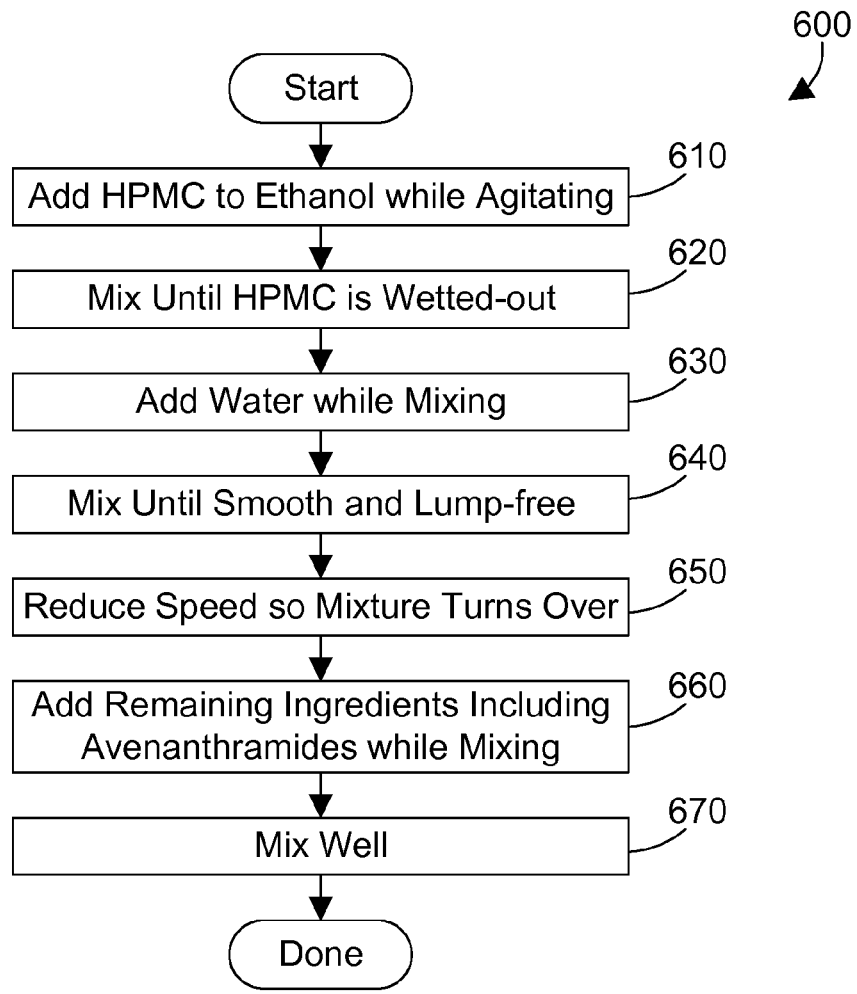
FIG. 6 is a flow diagram of a method for manufacturing an alcohol-based topical sanitizer that includes avenanthramides.

Referring to FIG. 6, a method 600 for making an alcohol-based topical sanitizer starts by adding Hydroxy Propyl Methyl Cellulose (HPMC) to ethanol while agitating to make a slurry (step 610). The mixture is mixed until the HPMC is wetted-out (step 620). Mixing for 10 minutes is normally sufficient to wet-out the HPMC. Water is then added to the slurry while mixing (step 630). The resulting mixture is then mixed until the mixture is smooth and lump-free (step 640). Mixing for 45 minutes is typically sufficient. The mixing speed is then reduced so the mixture "turns over" (step 650). Other ingredients including avenanthramides are added while mixing (step 660). The mixture is then mixed well (step 670). Mixing for 10 more minutes is typically sufficient. Because the ethanol can easily evaporate in an open system, the preferred mixing system used in method 600 is a closed system.

One form of avenanthramides that is commercially available is a product known as colloidal oat extract distributed by Ceapro, Inc., Suite 4174 Enterprise Square, 10320 Jasper Avenue, Edmonton, Alberta, Canada T5J 4P6. The colloidal oat extract is formulated to 100 parts per million (ppm) avenanthramides in a glycerin:water 1:1 base. For example, the colloidal oat extract could be made by preparing a solution of 10 mg avenanthramides in 50 grams of water and 50 grams of glycerin. Because the colloidal oat extract includes glycerin and water, the amount of colloidal oat extract to use in the formulations below can be determined mathematically from the avenanthramides concentration, which will result in a corresponding reduction in the amount of glycerin needed.

The specific ingredients and proportions for the alcohol-based sanitizing gel are preferably:

| | |
|---|---|
| Ethanol (Absolute Ethyl alcohol) | >62 grams |
| Glycerin | >0.1 grams |
| Vitamin E USP (DL-alpha tocopheryl acetate) | >0.1 grams |
| Hydroxy Propyl Methyl Cellulose (HPMC) | >1 grams |
| Avenanthramides | >0.3 ppm |
| Deionized water | balance to make 100 gram batch |

A suitable combination of these ranges will preferably sum to 100 grams, which means the numbers also express a percentage of each ingredient by weight in the gel. The alcohol-based sanitizing gel may also include zinc acetate. Zinc acetate is a proven skin protectant, and has received a USP monograph as a skin protectant. For the specific formulation above, a range of 0.1 to 2.0 grams of zinc acetate could be added to the mixture to enhance the skin-protecting properties of the alcohol-based sanitizer gel.

The specific ingredients and proportions for the alcohol-based sanitizing gel are more preferably:

| | |
|---|---|
| Ethanol (Absolute Ethyl alcohol) | 0.62-80 grams |
| Glycerin | 1.0-2.0 grams |
| Vitamin E USP (DL-alpha tocopheryl acetate) | 0.2-1.0 grams |
| Hydroxy Propyl Methyl Cellulose (HPMC) | 1.0-1.75 grams |
| Avenanthramides | 0.4-10 ppm |
| Deionized water | balance to make 100 gram batch |

Zinc acetate could also be added to this formulation. A range of 0.1 to 0.5 grams of zinc acetate could be added to the mixture to enhance the skin-protecting properties of the alcohol-based sanitizer gel.

The specific ingredients and proportions for the alcohol-based sanitizing gel are most preferably:

| | |
|---|---|
| Ethanol (Absolute Ethyl alcohol) | 65.00 grams |
| Glycerin | 1.50 grams |
| Vitamin E USP (DL-alpha tocopheryl acetate) | 0.5 grams |
| Hydroxy Propyl Methyl Cellulose (HPMC) | 1.50 grams |
| Avenanthramides | 1.0 ppm |
| Deionized water | balance to make 100 gram batch |

Note these ingredients sum to 100 grams, which means the numbers also express a percentage of each ingredient by weight in the gel. Zinc acetate could also be added to this formulation. The most preferred proportion of zinc acetate is 0.2 percent by weight of the alcohol-based sanitizer gel. Note the addition of zinc acetate will require a corresponding reduction in one of the other ingredients to keep the total weight of the formulation at 100 grams, so the numbers still reflect percent by weight of the total. In this most preferred implementation, the amount of deionized water is reduced to account for the addition of the zinc acetate. Because zinc is a skin protectant, adding zinc acetate to the alcohol-based sanitizer gel allows the alcohol-based sanitizer gel to claim skin protectant properties.

Figure 7:
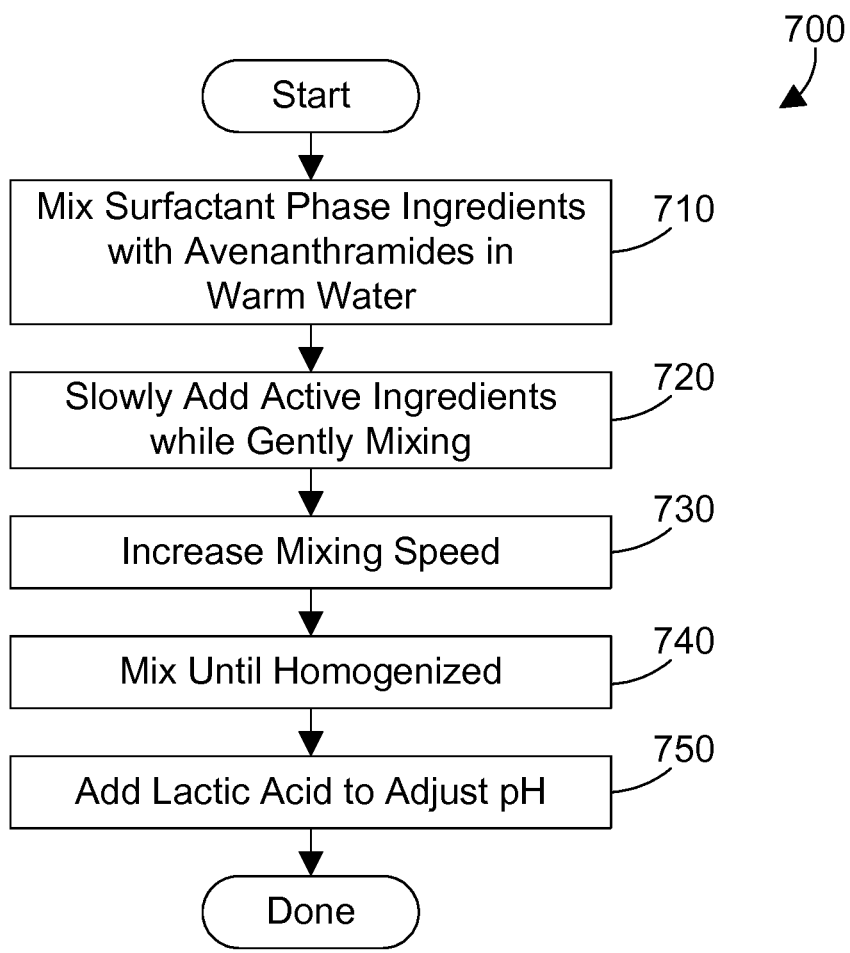
FIG. 7 is a flow diagram of a method for manufacturing a foam soap topical sanitizer or alcohol-free sanitizing foam topical sanitizer that includes avenanthramides.

A second specific embodiment of the topical sanitizer is a foam soap that includes avenanthramides. A method 700 in FIG. 7 represents a method that may be used to make foam soap. Method 700 begins by premixing the surfactant phase ingredients, specifically the PEG-80 sorbitan laurate, sodium trideceth sulfate, cocamidopropyl betaine, and PEG-150 distearate in a suitable volume of water, such as 50 grams, warmed preferably to a temperature of 35 to 45° C. (step 710). The active ingredients including the avenanthramides, and vitamin E are then added slowly to the warm water while gently mixing (step 720). The mixing speed is increased to homogenize the mixture (step 730). Mixing continues until the mixture is homogenized (step 740). Lactic acid is then added to adjust the pH of the mixture (step 750). The quantity of lactic acid may vary due to variations in the other ingredients. The pH has a preferred range of 4.0 to 6.0, has a more preferred range of 4.5 to 5.5, and is most preferably approximately 5.0.

The specific ingredients and proportions for the foam soap are preferably:

| | |
|---|---|
| PEG-80 sorbitan laurate | 5-40 grams |
| Sodium trideceth sulfate | 5-40 grams |
| Cocamidopropyl betaine | 1-10 grams |
| PEG-150 distearate | >1 gram |
| Avenanthramides | >0.4 ppm |
| Vitamin E USP (DL-alpha tocopheryl acetate) | >0.1 grams |
| Lactic acid (90%) | q.s. |
| Deionized water | balance to make 100 gram batch |

In accordance with method 700 in FIG. 7, the PEG-80 sorbitan laurate, sodium trideceth sulfate, and cocamidopropyl betaine are premixed with a suitable quantity (such as 50 grams) of water in step 710 and gently mixed. The active ingredients including avenanthramides and vitamin E are added and mixed (step 720). The mixing speed is then increased (step 730) and the batch is mixed until homogenized (step 740). Lactic acid is then added to adjust the pH (step 750). The quantity of lactic acid varies due to variability of the other ingredients. The term "q.s." used above to indicate the amount of lactic acid is known in the art to be an abbreviation for "Quantum Sufficiat", a Latin term meaning a sufficient quantity. Once enough lactic acid has been added to achieve the desired pH, water is added to bring the batch to 100 grams total weight.

A suitable combination of these ranges will preferably sum to 100 grams, which means the numbers also express a percentage of each ingredient by weight in the foam soap. Zinc acetate could also be added to this formulation. The preferred proportion of zinc acetate is 0.1-2.0 percent by weight of the foam soap. The more preferred proportion of zinc acetate is 0.1-0.5 percent by weight of the foam soap. The most preferred proportion of zinc acetate is 0.2 percent by weight of the foam soap.

The specific ingredients and proportions for the foam soap are more preferably:

| | |
|---|---|
| PEG-80 sorbitan laurate | 10-30 grams |
| Sodium trideceth sulfate | 10-30 grams |
| Cocamidopropyl betaine | 2-15 grams |
| PEG-150 distearate | 1-10 grams |
| Avenanthramides | 0.4-10 ppm |
| Vitamin E USP (DL-alpha tocopheryl acetate) | 0.2-1.0 grams |
| Lactic acid (90%) | q.s. |
| Deionized water | balance to make 100 gram batch |

As above, zinc acetate could also be added to provide skin protectant properties for the foam soap in the ranges or specific proportion discussed above.

The specific ingredients and proportions for the foam soap are most preferably:

| | |
|---|---|
| PEG-80 sorbitan laurate | 15 grams |
| Sodium trideceth sulfate | 15 grams |
| Cocamidopropyl betaine | 3.33 grams |
| PEG-150 distearate | 1.6 grams |
| Avenanthramides | 1.0 ppm |
| Vitamin E USP (DL-alpha tocopheryl acetate) | 0.5 grams |
| Lactic acid (90%) | q.s. |
| Deionized water | balance to make 100 gram batch |

As above, zinc acetate could also be added to provide skin protectant properties for the foam soap in the ranges or specific proportion discussed above. For the proportions shown above, 0.20 grams of zinc acetate is added, with a corresponding reduction in the amount of water by 0.20 grams to keep the total at 100 grams so the proportions reflect percentages by weight in the foam soap.

Figure 8:
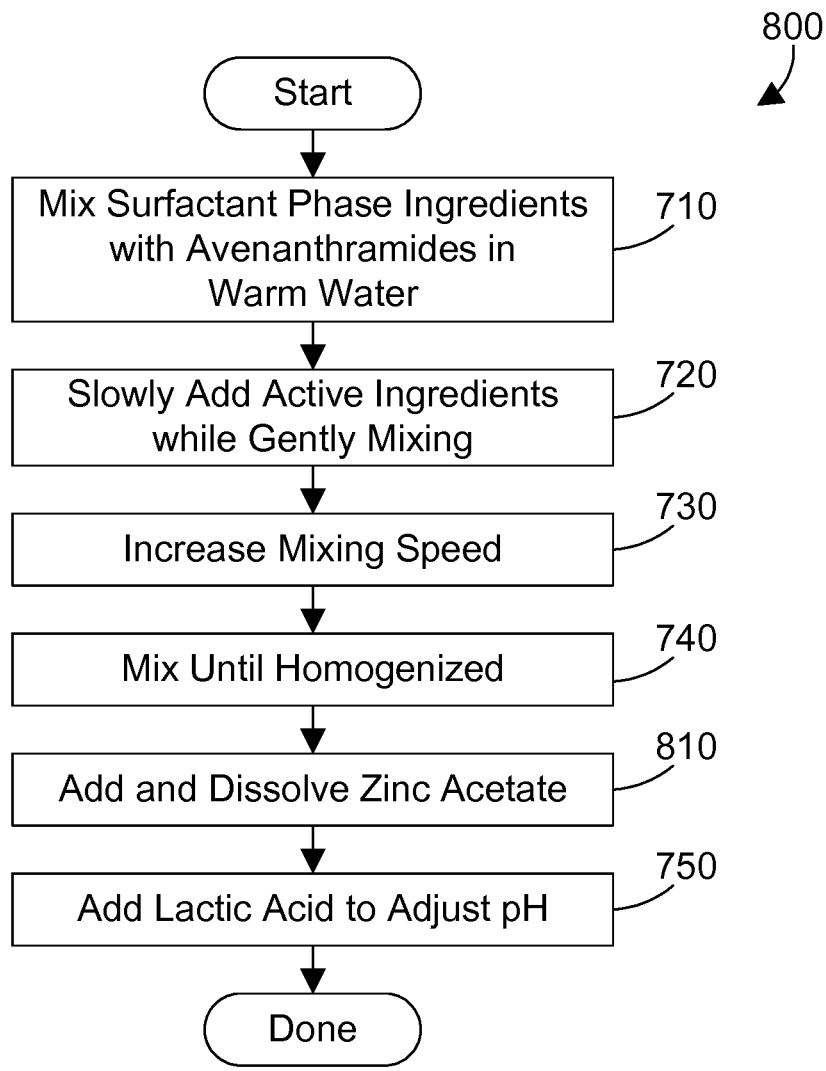
FIG. 8 is a flow diagram of a method for manufacturing a foam soap topical sanitizer or alcohol-free sanitizing foam topical sanitizer that includes avenanthramides and zinc acetate.

Method 800 in FIG. 8 shows one suitable method for including zinc acetate in the foam soap. The steps 710, 720, 730, 740 and 750 are the same as the steps shown in FIG. 7. The difference in FIG. 8 is the addition of the zinc acetate in step 810. Because zinc acetate is a skin protectant, adding zinc acetate to the foam soap allows the foam soap to claim skin protectant properties.

The methods shown in FIGS. 7 and 8 may also be used to manufacture an alcohol-free sanitizing foam. While the process is similar, the specific ingredients and their proportions are different. One ingredient that is added is benzalkonium chloride, which is available under the name Nobac from Mason Chemical Co., 721 West Algonquin Road, Arlington Heights, Ill. 60005. The specific ingredients and proportions for the alcohol-free sanitizing foam are preferably:

| | |
|---|---|
| PEG-80 sorbitan laurate | 0.83-6.67 grams |
| Sodium trideceth sulfate | 0.83-6.67 grams |
| Cocamidopropyl betaine | 0.16-1.67 grams |
| PEG-150 distearate | >0.16 grams |
| Avenanthramides | >0.4 ppm |
| Vitamin E USP (DL-alpha tocopheryl acetate) | >0.1 grams |
| Benzalkonium Chloride | 0.1-1.0 grams |
| Lactic acid (90%) | q.s. |
| Deionized water | balance to make 100 gram batch |

A suitable combination of these ranges will preferably sum to 100 grams, which means the numbers also express a percentage of each ingredient by weight in the foam soap. Zinc acetate could also be added to this formulation. The preferred proportion of zinc acetate is 0.1-2.0 percent by weight of the alcohol-free sanitizing foam. The more preferred proportion of zinc acetate is 0.1-0.5 percent by weight of the alcohol-free sanitizing foam. The most preferred proportion of zinc acetate is 0.2 percent by weight of the alcohol-free sanitizing foam.

The specific ingredients and proportions for the alcohol-free sanitizing foam are more preferably:

| | |
|---|---|
| PEG-80 sorbitan laurate | 1.67-5.0 grams |
| Sodium trideceth sulfate | 1.67-5.0 grams |
| Cocamidopropyl betaine | 0.33-2.5 grams |
| PEG-150 | 0.16-1.6 grams |
| Avenanthramides | 0.4-10 ppm |
| Vitamin E USP (DL-alpha tocopheryl acetate) | 0.2-1.0 grams |
| Benzalkonium Chloride | 0.1-0.2 grams |
| Lactic acid (90%) | q.s. |
| Deionized water | balance to make 100 gram batch |

As above, zinc acetate could also be added to provide skin protectant properties for the foam soap in the ranges or specific proportion discussed above.

The specific ingredients and proportions for the alcohol-free sanitizing foam are most preferably:

| | |
|---|---|
| PEG-80 sorbitan laurate | 2.5 grams |
| Sodium trideceth sulfate | 2.5 grams |
| Cocamidopropyl betaine | 0.55 grams |
| PEG-150 distearate | 0.27 grams |
| Avenanthramides | 1.0 ppm |
| Vitamin E USP (DL-alpha tocopheryl acetate) | 0.5 grams |
| Benzalkonium Chloride | 0.13 grams |
| Lactic acid (90%) | q.s. |
| Deionized water | balance to make 100 gram batch |

As stated above, zinc acetate could also be added to this alcohol-free sanitizing foam in the ranges or specific proportion discussed above. For the proportions shown above, 0.20 grams of zinc acetate is added, with a corresponding reduction in the amount of water by 0.20 grams to keep the total at 100 grams so the proportions reflect percentages by weight in the alcohol-free sanitizing foam.

Figure 9:
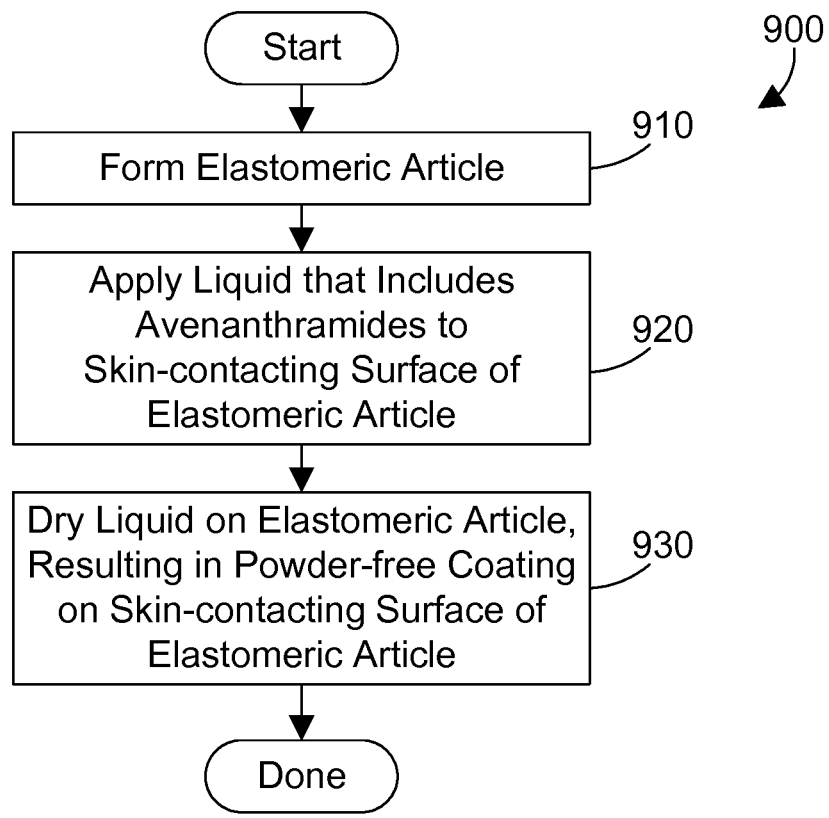
FIG. 9 is a flow diagram of a method for manufacturing an elastomeric article such as a glove with a coating that includes avenanthramides on the skin-contacting surface of the article.

The topical sanitizers disclosed herein, namely the alcohol-based sanitizing gel, the foam soap, and the alcohol-free sanitizing form, may be used in conjunction with gloves that have a coating that includes avenanthramides and optionally includes zinc acetate so the gloves provide skin conditioning and protecting properties to the hands of the wearer of the gloves. Referring to FIG. 9, a method 900 shows how such gloves may be manufactured. First, the elastomeric article is formed (step 910). A glove is one suitable example of an elastomeric article. A liquid that includes avenanthramides is then applied to the skin-contacting interior surface of the elastomeric article (step 920). Note the liquid applied in step 920 could optionally include zinc acetate, which provide skin protecting properties to the liquid. The liquid is then dried, resulting in a powder-free coating on the skin-contacting surface of the elastomeric article (step 930). When gloves are manufactured in accordance with method 900 in FIG. 9, wearing the gloves imparts the avenanthramides (and zinc, if present) to the skin on the hands of the person wearing the gloves. Because avenanthramides are the active ingredients in oats that provide the well-documented benefits of oats, such gloves are greatly beneficial to the skin. However, using gloves with avenanthramides solves only part of the problem. When a person takes off the gloves and washes his or her hands, the avenanthramides that were put onto the hands by the gloves may be reduced by washing. However, using one of the topical sanitizers disclosed herein results in avenanthramides (and zinc, if present) being available on the skin during the entire workday, both while wearing the gloves and after removing the gloves. Note the mechanical rubbing in of the topical sanitizers enhances the application and penetration of the avenanthramides into the skin, further enhancing the hand protective performance of the topical sanitizers.

Method 900 in FIG. 9 may be used to provide a coating that includes avenanthramides on the inner surface of disposable gloves. However, the disclosure and claims herein expressly extend to non-disposable gloves as well. Non-disposable gloves may benefit from an inner coating that includes avenanthramides and optionally includes zinc acetate. For example, a spray that includes avenanthramides could be used to spray the interior of a non-disposable glove. Examples of suitable non-disposable gloves that could benefit from an inner coating that includes avenanthramides and optionally includes zinc acetate include: leather work gloves, sports gloves (including baseball mitts, batting gloves, boxing gloves, racquetball gloves, weight lifting gloves, tennis gloves, golf gloves, hockey gloves, etc.), welding gloves, chemical protection gloves, gardening gloves, etc.

Figure 10:
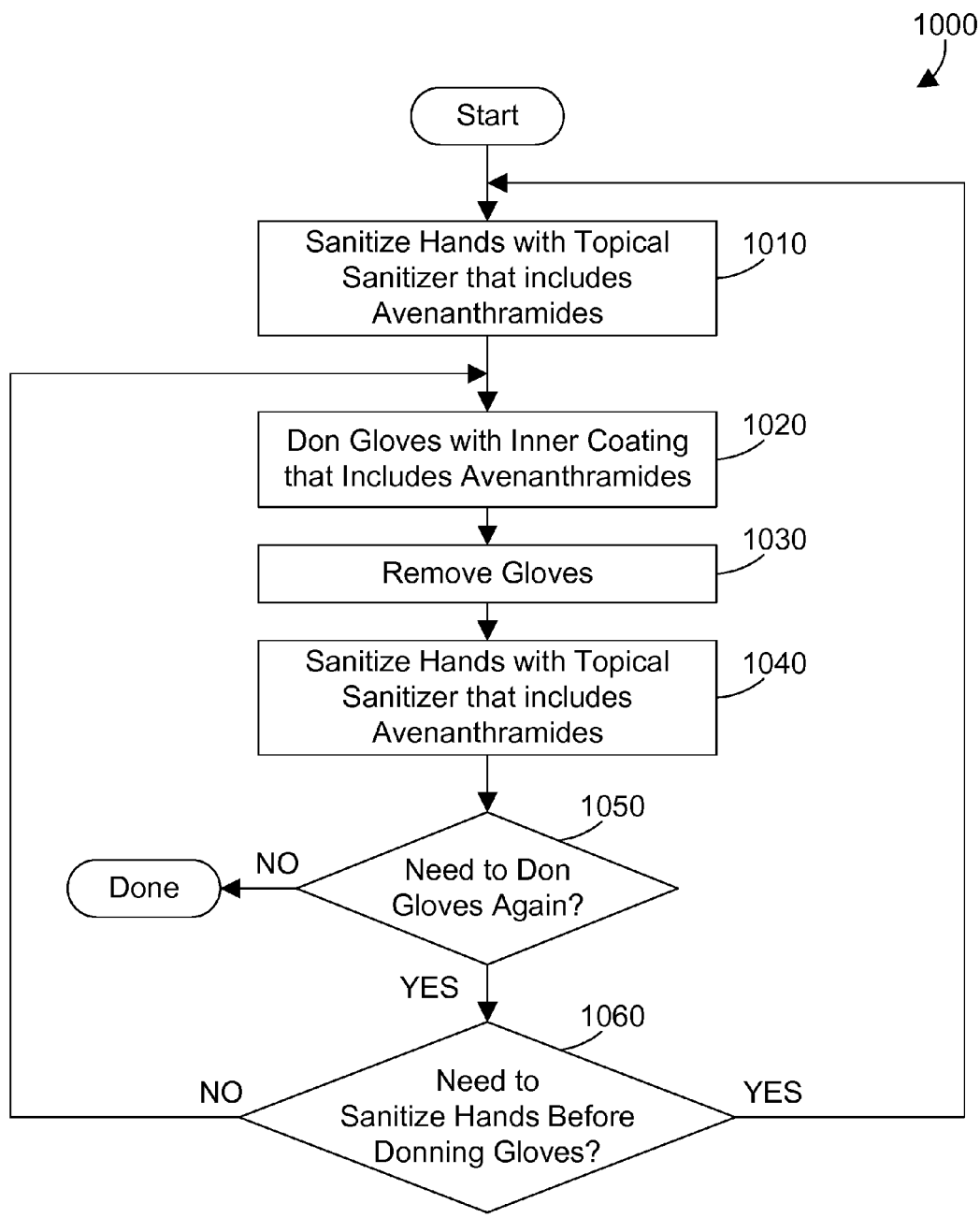
FIG. 10 is a flow diagram of a method for using topical sanitizer that includes avenanthramides in conjunction with gloves that have an inner coating that includes avenanthramides.

By providing both topical sanitizers and gloves that include avenanthramides, a new level of hand protection and treatment is available to those who wear gloves extensively. Referring to FIG. 10, a method 1000 for conditioning skin on hands begins when a person sanitizers his or her hands with a topical sanitizer that includes avenanthramides (step 1010). The person may then don gloves that include an inner coating that includes avenanthramides (step 1020). The person then removes the gloves (step 1030), and typically discards the gloves. The person may then sanitize his or her hands with a topical sanitizer that includes avenanthramides (step 1040). If the person does not need to don gloves again (step 1050=NO), method 1000 is done. If the person needs to don gloves again (step 1050=YES), a determination is made whether the person needs to sanitize his or her hands again before donning the gloves (step 1060). This determination may be made according to government health mandates, according to standard practices in the industry, according to company policy, or according to instructions provided with the topical sanitizer and gloves. For example, if the person just removed gloves in step 1030 and sanitized her hands in step 1040 and immediately needs to don gloves again, there may be no need to sanitize the hands again before donning a new pair of gloves (step 1060=NO). If there is no need to sanitize the hands again before donning a new pair of gloves (step 1060=NO), method 1000 loops back to step 1020 and continues. If, however, the person sanitized her hands in step 1040 some time ago, she may need to sanitizer her hands again before donning a new pair of gloves (step 1060=YES). In this case, method 1000 loops back to step 1010 and continues. Note that a person could use different topical sanitizers in steps 1010 and 1040 according to their location and convenience. Thus, if a doctor is sanitizing her hands before examining a patient in her office, she may use the alcohol-based sanitizing gel from a bottle available in her office. If the doctor is scrubbing up for surgery, the doctor may use the foam soap. If the doctor is making rounds in a hospital, the doctor may use the alcohol-free sanitizing foam from a belt dispenser or wristband dispenser. Method 1000 illustrates that regardless of how many times a person changes gloves and has to sanitize his or her hands, that person can enjoy the benefits of avenanthramides, and optionally zinc, on their hands throughout the day, both when they are wearing gloves and after taking the gloves off.

Figure 11:
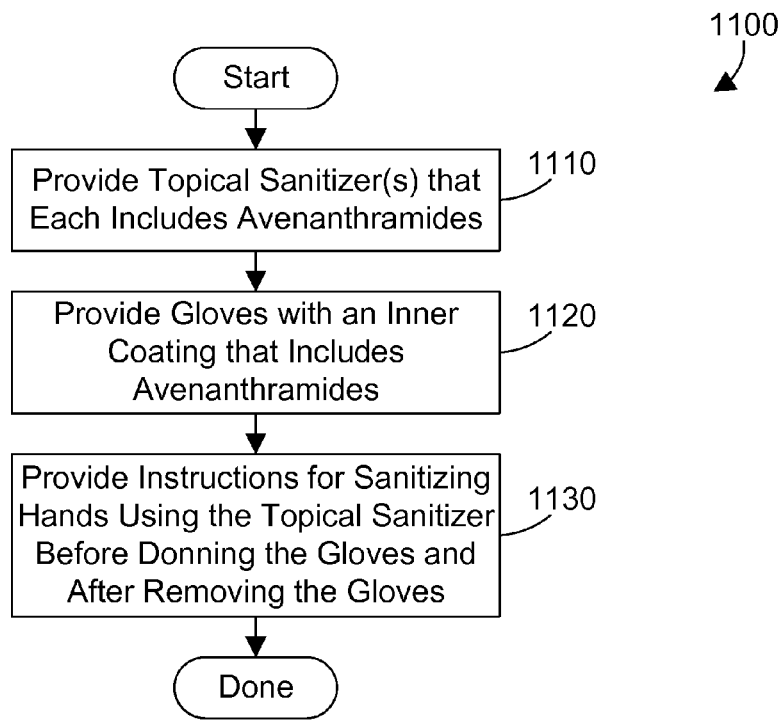
FIG. 11 is a flow diagram of a method for conditioning skin on hands.

A method for conditioning skin as shown in the detailed steps in FIG. 10 is made possible by method 1100 in FIG. 11. First, provide one or more topical sanitizers that include avenanthramides (step 1110). Next, provide gloves with an inner coating that includes avenanthramides (step 1120). Then provide instructions for sanitizing hands using the topical sanitizer(s) before donning the gloves and after removing the gloves (step 1100). The method for conditioning skin and a corresponding hand care system as described herein may include a single topical sanitizer or may include multiple topical sanitizers. For the specific examples given herein, the hand care system may include one, two or all three of the topical sanitizers disclosed herein, namely alcohol-based sanitizing gel, foam soap, and alcohol-free sanitizing foam.

Figure 12:
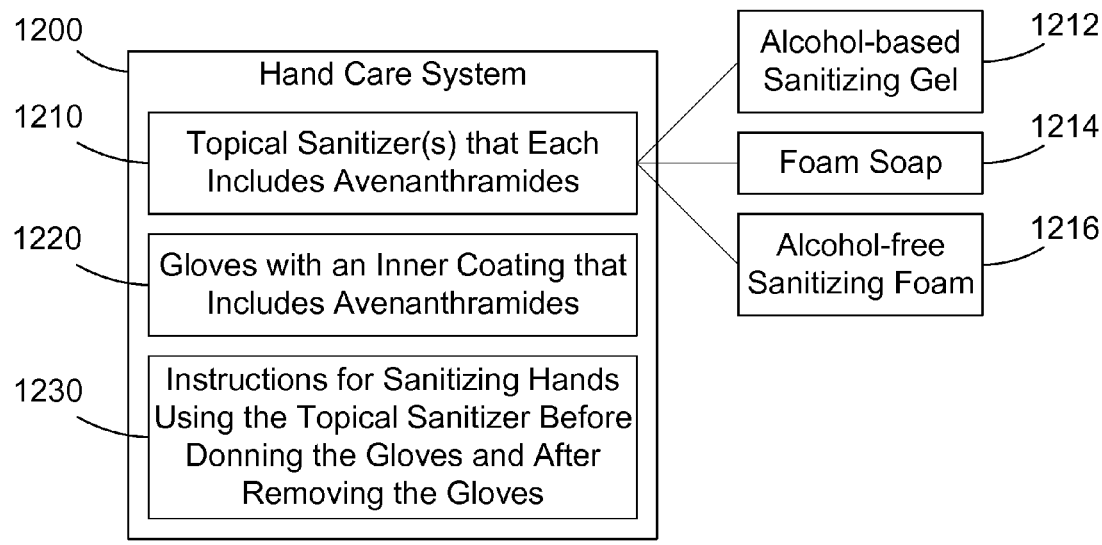
FIG. 12 is a block diagram of a hand care system.

The result of providing both topical sanitizers that include avenanthramides and gloves that include avenanthramides is an overall hand care system that allows the beneficial avenanthramides to be in contact with a person's skin on their hands during the entire workday. Such a hand care system is shown in block diagram form in FIG. 12. The hand care system 1200 includes one or more topical sanitizers 1210 that each includes avenanthramides. For the specific examples detailed above, these include alcohol-based sanitizing gel 1212, foam soap 1214, and alcohol-free sanitizing foam 1216. The hand care system 1200 further includes gloves 1220 with an inner coating that includes avenanthramides. The hand care system 1200 further includes instructions 1230 for sanitizing hands using the topical sanitizer(s) before donning the gloves and after removing the gloves.

The specific formulations above are given by way of example. Many variations are possible within the scope of the disclosure and claims herein, which expressly extend to any suitable formulation that includes avenanthramides and optionally includes zinc acetate.

The topical sanitizers and hand care system disclosed herein provide significant advantages over currently-known methods discussed above. By allowing avenanthramides to be in constant contact with a person's skin using the topical sanitizers, methods and hand care system herein, the skin on the person's hands will be more soft and any skin irritation will be greatly reduced. The result is much greater comfort to the hands of those who wear gloves extensively.

One skilled in the art will appreciate that many variations are possible within the scope of the claims. Thus, while the disclosure is particularly shown and described above, it will be understood by those skilled in the art that these and other changes in form and details may be made therein without departing from the spirit and scope of the claims.

The invention claimed is:

1. A sanitizing gel comprising:
   ethanol that is approximately 65% by weight of the sanitizing gel;
   hydroxyl propyl methyl cellulose that is approximately 1.5% by weight of the sanitizing gel;
   avenanthramides that are approximately 1.0 parts per million by weight of the sanitizing gel;
   glycerin that is approximately 1.5% by weight of the sanitizing gel; and
   vitamin E that is approximately 0.5% by weight of the sanitizing gel.

2. The sanitizing gel of claim 1 further comprising zinc acetate.

3. The sanitizing gel of claim 1 further comprising water.

4. A sanitizing gel comprising:
   water that is approximately 31.05% by weight of the sanitizing gel;
   ethanol that is approximately 65% by weight of the sanitizing gel;
   hydroxyl propyl methyl cellulose that is approximately 1.5% by weight of the sanitizing gel;
   avenanthramides that are approximately 1.0 parts per million by weight of the sanitizing gel;
   glycerin that is approximately 1.5% by weight of the sanitizing gel;
   vitamin E that is approximately 0.5% by weight of the sanitizing gel; and
   zinc acetate that is approximately 0.20% by weight of the sanitizing gel.

* * * * *